US00PP20434P3

(12) United States Plant Patent
Delabroye

(10) Patent No.: US PP20,434 P3
(45) Date of Patent: Oct. 20, 2009

(54) ***HEUCHERA* PLANT NAMED 'PINOT NOIR'**

(50) Latin Name: ***Heuchera* hybrid**
Varietal Denomination: Pinot Noir

(76) Inventor: Sandrine Delabroye, Rue Roger Salengro 40, Hantay (FR) F-59496

( * ) Notice: Subject to any disclaimer, the term of this patent is extended or adjusted under 35 U.S.C. 154(b) by 45 days.

(21) Appl. No.: 12/002,889

(22) Filed: Dec. 19, 2007

(65) Prior Publication Data

US 2009/0165181 P1 Jun. 25, 2009

(51) Int. Cl.
*A01H 5/00* (2006.01)

(52) U.S. Cl. ..... Plt./440

(58) Field of Classification Search ..... Plt./440
See application file for complete search history.

*Primary Examiner*—June Hwu
(74) *Attorney, Agent, or Firm*—Penny J. Aguirre

(57) ABSTRACT

A new cultivar of *Heuchera* of hybrid origin, 'Pinot Noir', characterized by its relatively small, broadly ovate shaped leaves held on purple petioles that are dark purple-grey in color when they emerge and developing a silver overlay with dark purple veins as they mature. 'Pinot Noir' is further characterized by its mounded and compact plant habit, its tolerance to high heat and humidity, its vigorous growth habit, its early blooming habit with abundant, creamy white flowers and its hardiness in U.S.D.A. Zones 4 to 9.

3 Drawing Sheets

Botanical classification: *Heuchera* hybrid.
Cultivar designation: 'Pinot Noir'.

CROSS REFERENCE TO A RELATED APPLICATION

This application is co-pending with U.S. Plant Patent applications filed for sibling plants derived from the same cross in the inventor's breeding program that are entitled *Heuchera* Plant Named 'Beaujolais' (U.S. Plant Pat. No. 19,577), *Heuchera* Plant Named 'Encore' (U.S. Plant Pat. No. 19,578), *Heuchera* Plant Named 'Pinot Gris' (U.S. Plant Pat. No. 19,592), *Heuchera* Plant Named 'Tiramisu' (U.S. Plant patent application Ser. No. 12/008,921 and *Heuchera* Plant Named 'Pistache' (U.S. Plant Pat. No. 19,585).

BACKGROUND OF THE INVENTION

The present invention relates to a new and distinct cultivar of hybrid *Heuchera,* botanically known as a *Heuchera* of hybrid origin and is hereinafter referred to by the cultivar name 'Pinot Noir'.

The new cultivar was derived from a controlled breeding program by the inventor in Hantay, France. The inventor made a cross in summer of 2005 between *Heuchera* 'Gloire d'Orleans' (not patented, syn. *Heuchera*×*brizoides* 'Gloire d'Orleans') and *Heuchera*×*villosa* 'Caramel' (U.S. Plant Pat. No. 16,560). The goal of the breeding program was to obtain unique cultivars of *Heuchera* that combined the flowering habit of 'Gloire d'Orleans' with the vigor and unique foliage coloration of *Heuchera*×*villosa.* The inventor selected 'Pinot Noir' in 2006 as a single unique plant amongst the seedlings that resulted from the above cross.

Asexual reproduction of the new cultivar was first accomplished under direction of the inventor by in vitro propagation in Rijswijk, The Netherlands in winter of 2007. Asexual reproduction of the new cultivar by division and tissue culture has shown that the unique features are stable and reproduced true to type in successive generations.

SUMMARY OF THE INVENTION

The following traits have been repeatedly observed and represent the characteristics of the new cultivar. These attributes in combination distinguish 'Pinot Noir' as a new and unique cultivar of *Heuchera.*

1. 'Pinot Noir' exhibits uniquely colored foliage with leaves that are dark purple-grey in color when they emerge and developing a silver overlay with dark purple veins as they mature, leaves held on purple petioles.
2. 'Pinot Noir' exhibits cordate shaped leaves that are smaller in size in comparison to most ×*villosa* hybrids and its sibling cultivars.
3. 'Pinot Noir' exhibits a mounded and compact plant habit.
4. 'Pinot Noir' is tolerant to high heat and humidity imparted by a ×*villosa* as one of the parent plants.
5. 'Pinot Noir' is cold hardy in U.S.D.A. Zone 4 to 9.
6. 'Pinot Noir' has a vigorous growth habit.
7. 'Pinot Noir' is an early and abundant bloomer with creamy white flowers.

'Pinot Noir' is a unique *Heuchera* with more vigor, cold hardiness, and tolerance to heat and humidity than is typical for a dark foliaged *Heuchera.* 'Pinot Noir' differs from its parent plants in that 'Caramel' is a ×*villosa* hybrid and has foliage that is yellow-orange in color and Gloire d'Orleans is a ×*brizoides* hybrid with green foliage.

'Pinot Noir' can be compared to *Heuchera* 'Gypsy Dancer' (U.S. Plant Pat. No. 15,959) for its similar leaf color in summer, however 'Gypsy Dancer' blooms with light pink blossoms rather than creamy white and has foliage that exhibits greener veins. The closest comparison plants in overall leaf shape, habit, and performance are its sibling cultivars that differ in foliage coloration; 'Beaujolais' has burgundy-red leaves overlaid with silver, 'Encore' has rose-purple leaves, 'Pinot Gris' has leaves that emerge orange-yellow and mature to a rose color with a silvery overlay, 'Tiramisu' has foliage that is yellow-green with red mottling, and 'Pistache' has yellow-green leaves.

BRIEF DESCRIPTION OF THE DRAWING

The accompanying colored photographs illustrate the overall appearance and distinct characteristics of the new *Heuchera*. The photographs in FIG. 1.

Figure 1:
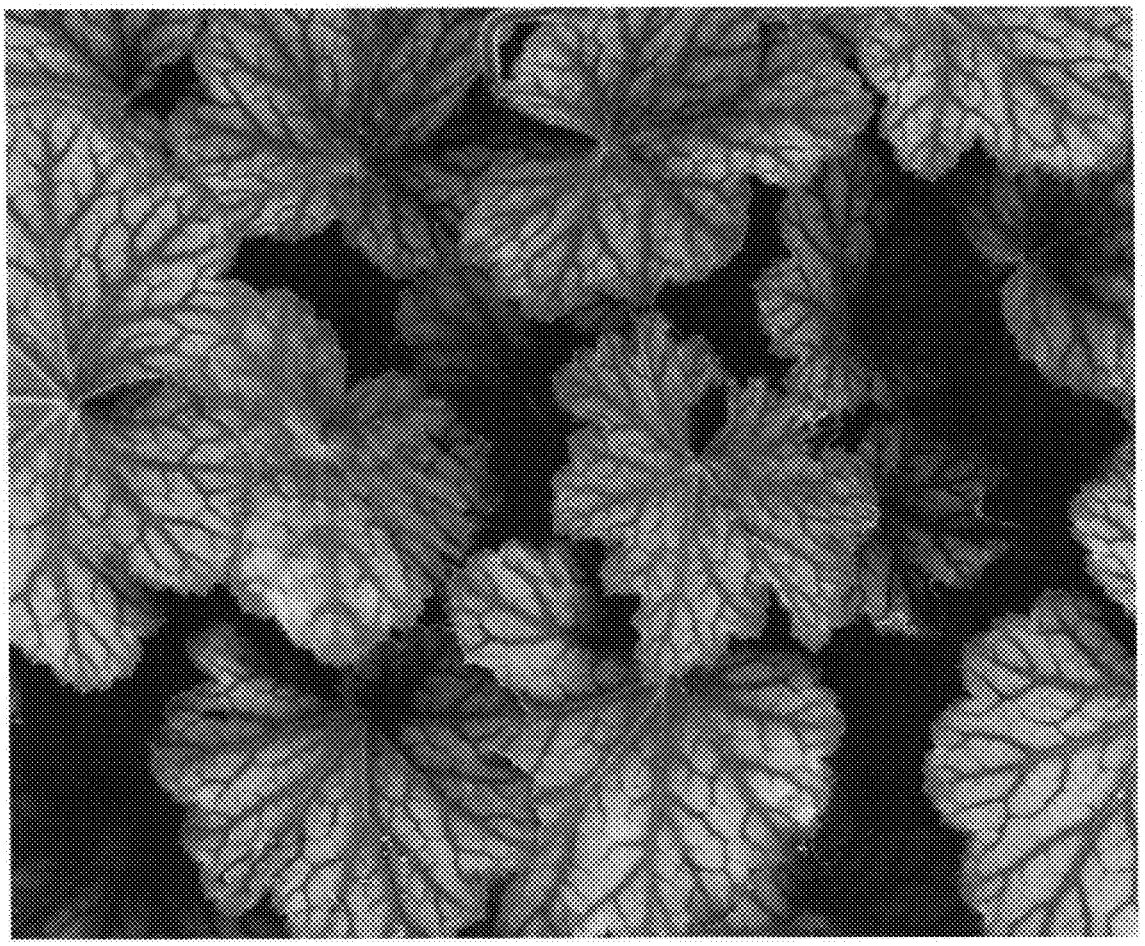

The photograph in FIG. 1 provides a view of the leaf form and typical mid summer coloration.

Figure 2:
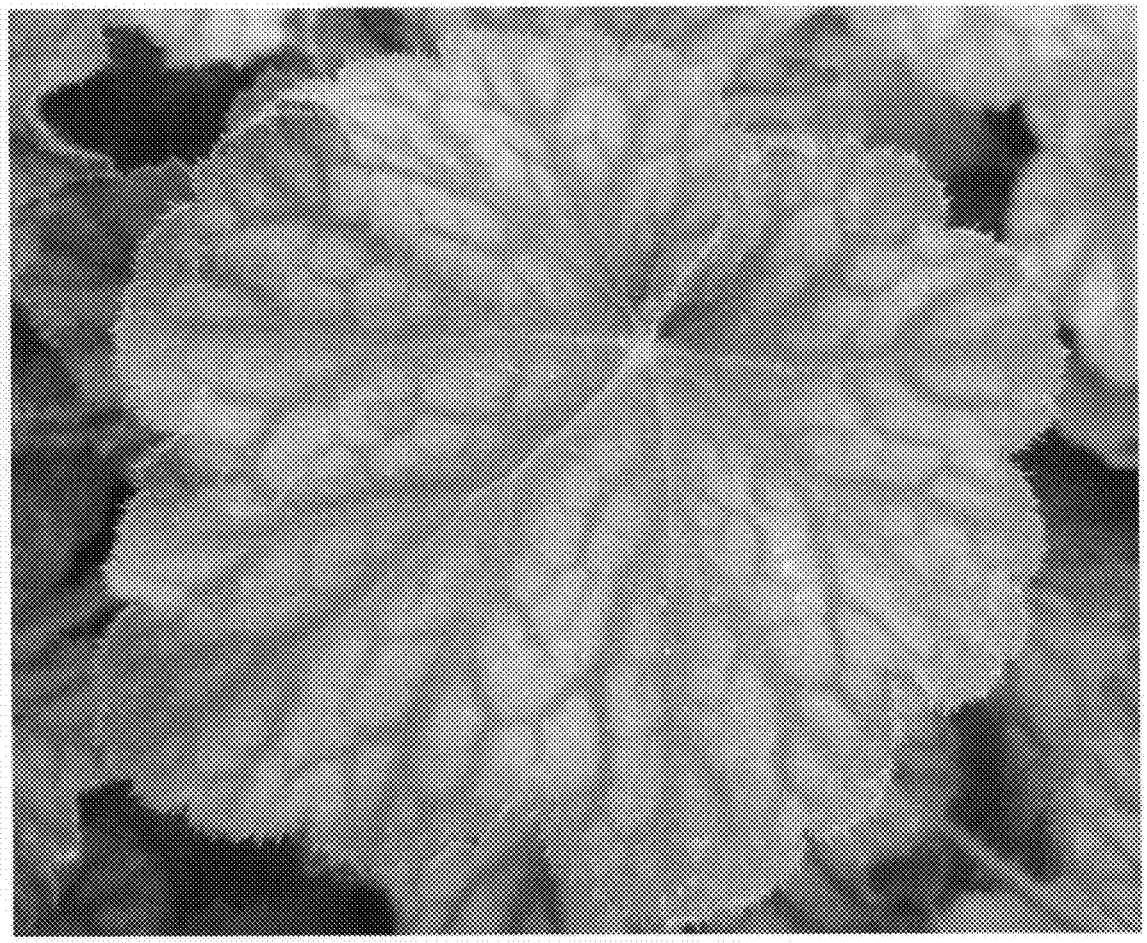
FIG. 2 were taken in mid summer of plants six months in age as grown outdoors in a trial garden in The Netherlands and the photographs in FIG. 3 and FIG. 4 were taken of plants two years in age as grown in a 2 gallon container in Hantay, France.

The photograph in FIG. 2 provides a close-up view of a leaf of 'Pinot Noir'.

Figure 3:
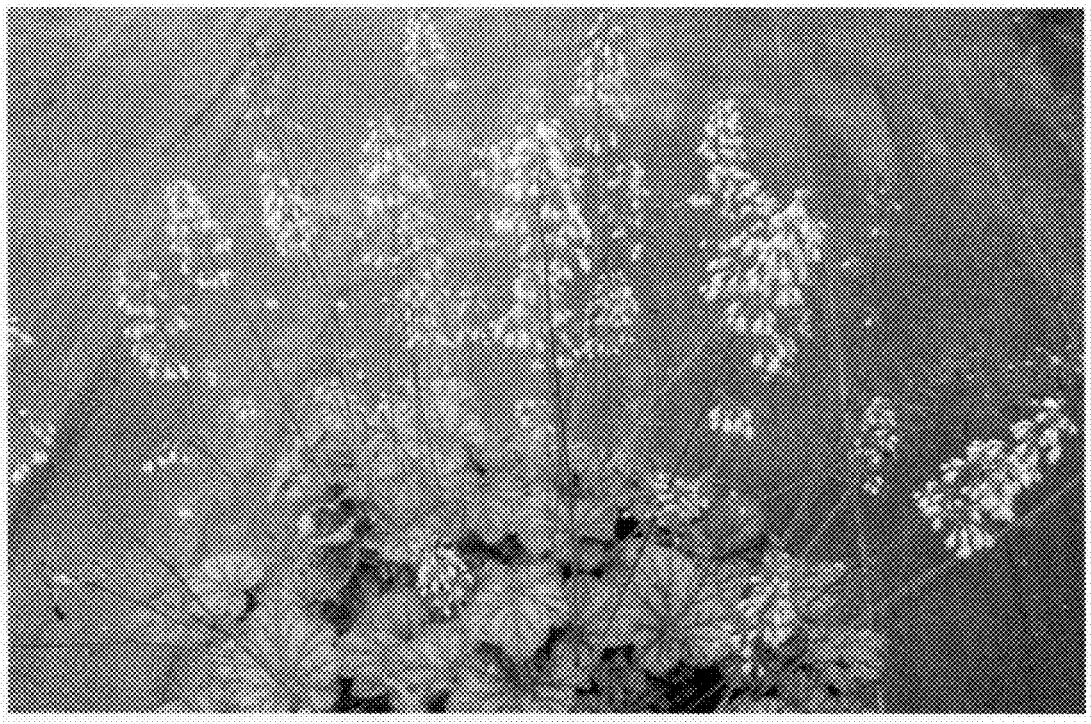

The photograph in FIG. 3 provides a side view in bloom of 'Pinot Noir'.

Figure 4:
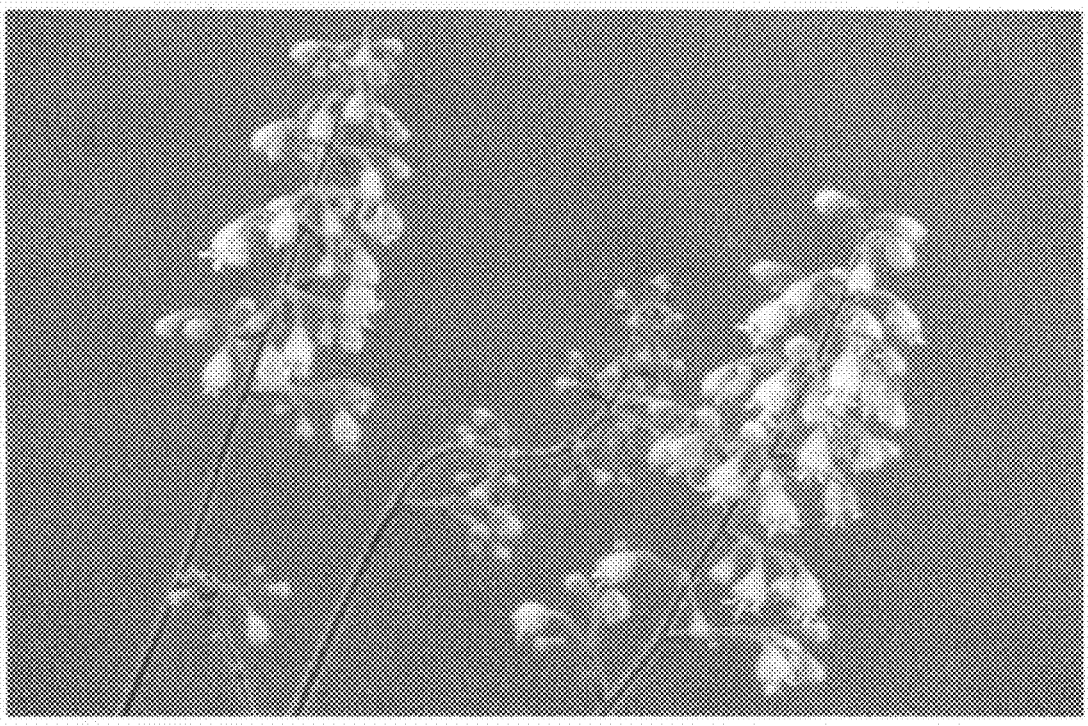

The photograph in FIG. 4 provides a close-up view of inflorescences of 'Pinot Noir'.

The colors in the photographs are as close as possible with the photographic and printing technology utilized. The color values cited in the detailed botanical description accurately describe the colors of the new *Heuchera*.

DETAILED BOTANICAL DESCRIPTION OF THE PLANT

The following is a detailed description of six month-old plants of the new cultivar as grown in 1-liter containers outdoors in New Hope, Minn. with the detailed flower data taken from plants two years in age as grown in two-gallon containers in Hantay, France. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

General description:

*Blooming period.*—About 5 weeks in early to mid summer.

*Plant habit.*—Compact, clump-forming herbaceous perennial, mounded foliage.

*Height and spread.*—Reaches about a height of about 25 cm in height and about 35 cm in width.

*Cold hardiness.*—U.S.D.A. Zones 4 to 9.

*Culture.*—Full sun to medium shade in moist, well-drained, fertile soils, tolerant to high heat and humidity.

*Diseases and pests.*—Disease free in the conditions tested, no susceptibility or resistance to pests has been observed.

*Root description.*—Fibrous roots on woody rootstalks.

*Branching habit.*—Basal rosettes of leaves on petioles.

*Propagation.*—In vitro propagation is the preferred method, division are also possible.

*Growth rate.*—Vigorous.

Foliage description:

*Leaf shape.*—Broadly ovate.

*Leaf division.*—Simple.

*Leaf base.*—Cordate, lobes overlapping.

*Leaf apex.*—Rounded to broadly acute.

*Leaf venation.*—Primarily palmate with reticulate secondary veins, conspicuous on upper and lower surface, palmate veins have stiff, short hairs about 1 mm in length.

*Leaf margins.*—Crenate with lobes (average of 6), not deeply parted.

*Leaf attachment.*—Petiolate.

*Leaf arrangement.*—Basal rosettes.

*Leaf orientation.*—Held nearly horizontal to petiole, held nearly flat to slightly concaved and slightly ruffled.

*Leaf surface.*—Finely pubescent on upper surface and puberulent on lower surface.

*Leaf color.*—Young leaves, upper and lower surface; N77C flushed with 191A at margins, mature leaves, upper surface; 191A with veins N79A to N79B, mature leaves, lower surface; 191A with veins 139A.

*Leaf size.*—Average of 6.7 cm in length and width.

*Leaf quantity.*—Average of 20 per 1-liter container.

*Petioles.*—Round in shape, average of 9 cm in length and 2 mm in width, N77D in color, surface is pubescent with abundant fine hairs 1 to 2 mm in length.

*Stipules.*—None.

Flower description:

*Inflorescence type.*—Numerous small bell-shaped flowers arranged on pyramidal panicles on flower scapes emerging from the base of the rosette, each peduncle has 2 pairs of lateral flowers and a terminal flower.

*Inflorescence size.*—An average of 9 cm in height and about 4.5 cm in width in full bloom.

*Inflorescence number.*—An average of 18 per 2-gallon container.

*Flower fragrance.*—None detected.

*Flower quantity.*—Average of 50 flowers per flowering stem.

*Flower lastingness.*—Average of 4 days per flower, individual panicles blooms for about 3 weeks, flowers persistent.

*Flower buds.*—Broadly elliptic in shape, an average of 2 mm in diameter and 3.5 mm in depth, 158B in color with apex 155B.

*Flower aspect.*—Drooping to slightly outward on peduncles held nearly horizontal to rachis.

*Flower type.*—Campanulate.

*Flower size.*—About 4 mm in diameter and 5.2 mm in depth.

*Petals.*—About 5, rotate arrangement and implanted in hypanthium at base, narrowly elliptic in shape, margin is entire, apex is narrowly apiculate, upper and lower surface is glabrous and dull, color of upper and lower surface when opening and mature is 155B, about 2.5 mm in length and 0.5 mm in width.

*Calyx.*—Campanulate, sepals fused to hypanthium, 2 mm in depth and 1.5 mm in diameter.

*Sepals.*—5, un-fused portion is elliptic in shape, about 2 mm in length and 0.5 mm in width, margin is entire, apex is acute, base is fused, surface villose, color of upper and lower surface is 160D in color.

*Bracts.*—None observed.

*Peduncles.*—Average of 3 cm in length and an average of 0.8 mm in width, held nearly horizontal to rachis, color 166A, surface is densely villose.

*Pedicels.*—Average of 2 mm in length and 0.3 mm in width, color 166A, villose surface, terminal is straight from peduncle and laterals are held at about a 45° angle.

*Rachis* (*flower scape*).—Average of 28 cm in length and an average of 2.5 mm in width, 166A in color, surface is villose, peduncle internode length is an average of 5 mm.

Reproductive organs:

*Gynoecium.*—2 Pistils, club-shaped, about 4.5 mm in length, stigmas minute and 155B in color, styles are about 4.5 mm in length and 155C in color, ovaries are superior and 144D in color.

*Androcoecium.*—About 5 stamens, anthers are ovate in shape, basifixed, about 0.3 mm in diameter and 155C in color, filaments are about 4 mm in length and 155C in color, no pollen was observed.

*Seed.*—None.

It is claimed:

1. A new and distinct cultivar of *Heuchera* plant named 'Pinot Noir' as herein illustrated and described.

* * * * *